United States Patent
Miller, Jr.

(10) Patent No.: US 6,192,883 B1
(45) Date of Patent: Feb. 27, 2001

(54) OXYGEN FLOW CONTROL SYSTEM AND METHOD

(76) Inventor: Richard L. Miller, Jr., P.O. Box 152, Myerstown, PA (US) 17067

( * ) Notice: Subject to any disclaimer, the term of this patent is extended or adjusted under 35 U.S.C. 154(b) by 0 days.

(21) Appl. No.: 09/366,622

(22) Filed: Aug. 3, 1999

(51) Int. Cl.⁷ .................................................. A61M 16/00
(52) U.S. Cl. ............................... 128/204.21; 128/204.23; 128/204.26; 128/205.24; 128/207.18
(58) Field of Search .................. 128/204.21, 204.23, 128/204.26, 205.24, 207.18

(56) References Cited

U.S. PATENT DOCUMENTS

| | | | |
|---|---|---|---|
| 3,788,310 | * 1/1974 | Fleischmann | 128/203.14 |
| 4,141,356 | * 2/1979 | Smargiassi | 128/204.26 |
| 4,165,738 | * 8/1979 | Graves et al. | 128/205.25 |
| 4,197,842 | 4/1980 | Anderson | 128/203.12 |
| 4,206,754 | * 6/1980 | Cox et al. | 128/204.26 |
| 4,380,233 | 4/1983 | Caillot | 128/204.21 |
| 4,393,869 | * 7/1983 | Boyarsky et al. | 128/204.21 |
| 4,413,622 | * 11/1983 | Austin | 128/205.25 |
| 4,457,304 | * 7/1984 | Molnar et al. | 128/205.24 |
| 4,461,293 | * 7/1984 | Chen | 128/204.23 |
| 4,510,930 | * 4/1985 | Garcia | 128/205.25 |
| 4,567,888 | 2/1986 | Robert et al. | 128/204.21 |
| 4,570,631 | * 2/1986 | Durkan | 128/204.23 |
| 4,619,269 | * 10/1986 | Cutler et al. | 128/205.12 |
| 4,681,099 | * 7/1987 | Sato et al. | 128/207.18 |
| 4,744,356 | 5/1988 | Greenwood | 128/204.26 |
| 5,024,219 | 6/1991 | Dietz | 128/204.21 |
| 5,072,737 | * 12/1991 | Goulding | 128/204.23 |
| 5,103,814 | * 4/1992 | Maher | 128/204.23 |
| 5,137,017 | 8/1992 | Salter | 128/207.18 |
| 5,188,098 | * 2/1993 | Hoffman et al. | 128/204.22 |
| 5,271,389 | 12/1993 | Isaza et al. | 128/204.21 |
| 5,315,990 | 5/1994 | Mondry | 128/205.11 |
| 5,323,772 | 6/1994 | Linden et al. | 128/204.23 |
| 5,365,922 | 11/1994 | Raemer | 128/204.23 |
| 5,388,575 | * 2/1995 | Taube | 128/204.23 |
| 5,390,666 | * 2/1995 | Kimm et al. | 128/204.23 |
| 5,577,496 | * 11/1996 | Blackwood et al. | 128/204.23 |
| 5,664,563 | 9/1997 | Schroeder et al. | 128/204.25 |
| 5,750,509 | 5/1998 | Lachmann et al. | 128/204.23 |
| 5,755,224 | * 5/1998 | Good et al. | 128/205.24 |
| 5,928,189 | 7/1999 | Phillips et al. | 604/65 |

* cited by examiner

Primary Examiner—Aaron J. Lewis
(74) Attorney, Agent, or Firm—Duane, Morris & Heckscher LLP (57) ABSTRACT

The present invention provides an oxygen control system for supplying a predetermined rate of flow from an oxygen source to a person in need of supplemental oxygen comprising an input manifold, an output manifold and a plurality of gas conduits interconnecting the input manifold to the output manifold. The oxygen source is arranged in flow communication with the input manifold, and a needle valve is positioned in flow control relation to each of the conduits so as to control the flow of oxygen from the input manifold to the output manifold. A plurality of solenoid valves, each having a first fully closed state corresponding to a preselected level of physical activity of the person and a second, fully open state corresponding to another preselected level of physical activity of the person, are positioned in flow control relation to all but one of the conduits. Sensors for monitoring the level of physical activity of the person are provided, along with a control system that is responsive to the monitored level of physical activity, for switching the solenoids between the first state and the second state. A method for supplying supplemental oxygen to a person according to the level of physical activity under taken by that person is also provided.

19 Claims, 4 Drawing Sheets

OXYGEN FLOW CONTROL SYSTEM AND METHOD

FIELD OF THE INVENTION

This invention relates to controlling oxygen flow from an oxygen reservoir to a person in need of supplemental oxygen, and more particularly to controlling the flow of oxygen supply in response to that person's physical activity level.

BACKGROUND OF THE INVENTION

In a healthy person, blood oxygen is automatically regulated through his or her respiration rate. As a person's activity level increases they breath faster and more deeply so that their respiratory system is able to deliver a greater amount of oxygen to their body. Diminished oxygen uptake into the body generally results from a partial disability of the pulmonary system, i.e., the lungs, caused by a variety of physiological ailments. Persons with pulmonary disabilities very often require enrichment of atmospherically available oxygen by artificial supplementation from a source of oxygen gas. The need for oxygen supplementation is particularly acute for persons suffering from Chronic Obstructive Pulmonary Disease (COPD) such as, emphysema.

In advanced COPD patients, the respiratory system is simply unable to supply the necessary oxygen levels required during increased activity. As a result, an acceptable level of oxygen must be maintained by enriching the oxygen level in the air being delivered to the lungs. This is often accomplished by placing a supply of oxygen at a central location and attaching one end of a long hose to the supply and the other to the patient. A common delivery system for supplemental oxygen is a tank reservoir containing pressurized medical quality oxygen. This type of tank is normally outfitted with a flow regulator comprising a flow control valve which governs the rate of oxygen flow, i.e., volume, from the tank to a nasal cannula, breathing mask, or transtracheal oxygen delivery system. With this type of conventional connection, the flow of gas is normally constant during both inhalation and exhalation.

The positioning of the control valve for the supply of oxygen at a distance from the patient has created problems in the art. Just as a healthy person's oxygen demand varies with the level of activity being undertaken, so does the demand for oxygen vary for COPD patients. The only way to deliver more oxygen to COPD patients, when such is required during periods of increased activity, i.e., walking to the bathroom, up steps, etc., has been to adjust the oxygen flow at the source prior to undertaking the activity. This has been accomplished either by the patient having to add the additional steps of walking to the oxygen source first, to adjust the flow and then carry on the activity, or to call to a family member or other person to assist them by increasing the flow. This causes logistical problems for the patient. Often, COPD patients merely maintain the flow rate of the oxygen at a higher level than necessary, i.e., during increased activity and at rest, which creates a dependency upon the higher oxygen levels that is similar in effect to the use of a habit forming drug.

In view of the large number of persons in society who require such oxygen supplementation, much effort has been dedicated to the development of devices which insure delivery of adequate supplemental oxygen. Exemplary prior art devices for detecting a patient's oxygen demand and providing for an increase in flow are disclosed in U.S. Pat. Nos: 4,567,888, issued to Robert, et al.; 4,744,356, issued to Greenwood; 5,024,219, issued to Dietz; 5,137,017, issued to Salter; 5,271,389, issued to Isaza, et al.; 5,315,990, issued to Mondry; 5,323,772, issued to Linden, et al.; 5,365,922, issued to Raemer; and 5,390,666, issued to Kimm, et al. Many of these devices rely upon sensors placed under the person's nose or otherwise on a person's face for detecting the flow of oxygen. Such sensors may prove irritating to the patient.

Some prior art systems employ a sensor connected to a controller which, in turn, is connected to a solenoid valve on an oxygen tank. Upon sensing inhalation, by pressure changes, etc., the sensor signals the controller to energize the solenoid, thus opening the valve and inducing oxygen flow. This arrangement may not provide oxygen to the user where there is a system failure or allow for a "ramp-down" period of gradual reduction in oxygen flow during a recovery period after increased activity. Also, these systems are used for the purpose of conserving oxygen rather than supporting the patient's need for varying levels of oxygen supply.

Other prior art oxygen delivery devices rely upon an oximeter to measure blood oxygen saturation. These devices adjust valves to deliver increased flow after oxygen saturation begins to decrease. Unfortunately, devices which rely upon a direct measure of blood oxygen levels are often found to be inadequate since the delivery of oxygen often falls behind the demand by the time required for the person's blood to circulate through the body. Also, these systems often rely upon the use of a finger sensor that is uncomfortable for the patient.

There is a need for an oxygen flow control device and method which provide increased oxygen flow rates to a patient, as needed, during increased activity, and which provides for "ramp-down" and "fail-safe" operation.

SUMMARY OF THE INVENTION

The present invention provides an oxygen control system for supplying a predetermined rate of flow from an oxygen source to a person in need of supplemental oxygen comprising an input manifold, an output manifold and a plurality of gas conduits interconnecting the input manifold to the output manifold. The oxygen source is arranged in flow communication with the input manifold, and a needle valve is positioned in flow control relation to each of the conduits so as to control the flow of oxygen from the input manifold to the output manifold. A plurality of solenoid valves, each having a first fully closed state corresponding to a preselected level of physical activity of the person and a second, fully open state corresponding to another preselected level of physical activity of the person, are positioned in flow control relation to all but one of the conduits. Advantageously, the solenoid valves are automatically placed in an open state when the system is unpowered. Means for monitoring the level of physical activity of the person are provided along with means that are responsive to the physical activity monitoring means for sequentially switching the solenoids between the first state and the second state according to a predetermined, timed sequence that corresponds to increases or decreases in physical activity.

A method is also provided for supplying supplemental oxygen to a person according to the level of physical activity under taken by that person comprising the steps of first providing a minimum flow of oxygen to the person and at least one clock to measure a plurality of sequential time periods. The person is then monitored during each of the sequential time periods in order to detect an increase in their physical activity level. If an increase in their physical activity level is detected, an additional flow of oxygen is provided to the person for a discrete period of time. When the increased level of physical activity subsides, the additional flow of oxygen is withdrawn from the person after the termination of the discrete period of time thus providing for a ramp down period.

BRIEF DESCRIPTION OF THE DRAWINGS

These and other features and advantages of the present invention will be more fully disclosed in, or rendered obvious by, the following detailed description of the preferred embodiments of the invention, which are to be considered together with the accompanying drawings wherein like numbers refer to like parts and further wherein.

DETAILED DESCRIPTION OF THE PREFERRED EMBODIMENTS

The following description of the preferred embodiments of the invention is intended to be read in connection with the foregoing drawings and is to be considered a portion of the entire written description of this invention. As used in the following description, terms such as, "horizonal", "vertical", "left", "right", "up", and "down", as well as adjectival and adverbial derivatives thereof (e.g., "horizontally", "rightwardly", "upwardly", etc.) simply refer to the orientation of the structure of the invention as it is illustrated in the particular drawing figure when that figure faces the reader. Similarly, the terms "inwardly"and "outwardly"generally refer to the orientation of a surface relative to its axis of elongation, or axis of rotation, as appropriate. Also, the terms "connected" and "interconnected," when used in this disclosure to describe the relationship between two or more structures, mean that such structures are secured or attached to each other either directly or indirectly through intervening structures, and include pivotal connections. The term "operatively interconnected" means that the foregoing direct or indirect connection between the structures allows such structures to operate as intended by virtue of such connection.

Referring to FIGS. 1–4, an oxygen flow control system 5 comprises means for controlling the flow of oxygen 8, means for sensing patient motion 10, and a source of supplemental oxygen gas 15. More particularly, and referring to FIG. 3, in one embodiment of the invention means for controlling the flow of oxygen 8 preferably include an input manifold 25, an output manifold 30, three gas conduits 35A,35B,35C, three needle valves 40A,40B,40C, two solenoid valves 45A,45C, and a programmable controller 50.

Figure 3:
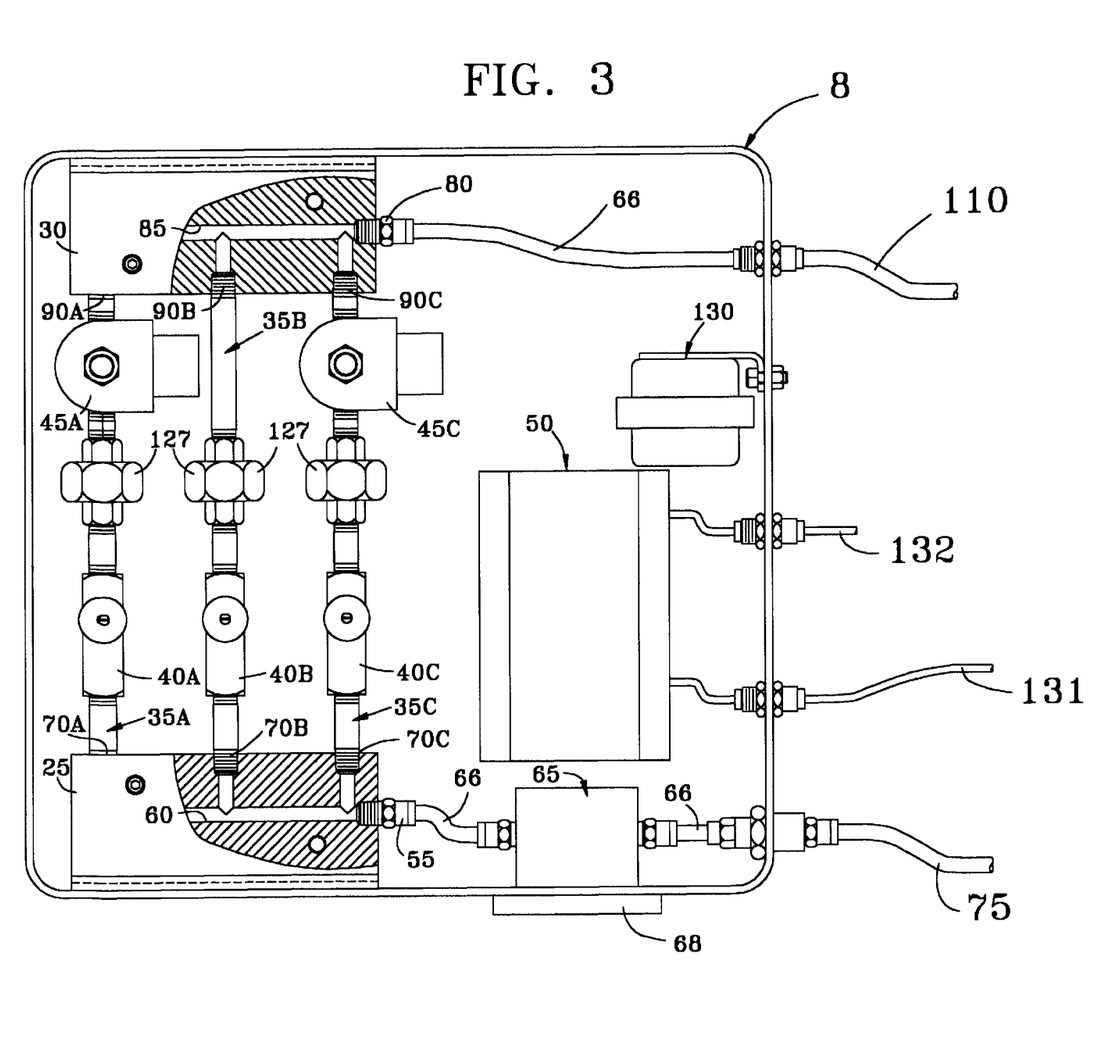
FIG. 3 is a plan view of the internal structures of the oxygen flow control system shown in FIG. 2.

Input manifold 25 comprises a gas input port 55 disposed in flow communication with a gas distribution tunnel 60. Three output ports 70A,70B,70C are also disposed in flow communication with gas distribution tunnel 60. Typically, gas input port 55 is interconnected to an oxygen flow gauge 65 by intermediate conduit 66, and to oxygen gas source 15 by an elongate tubular conduit 75, both of the type well known in the art for providing COPD patients with their required flow of oxygen. For example, oxygen source 15 may be a high pressure oxygen gas source, liquid oxygen, an oxygen concentrator, etc. Oxygen flow gauge 65 is of the type well known for measuring the rate of flow of a gas, and includes a display panel and indicator 68. Tubular conduit 75 may be 10 to 15 meters or more in length.

Output manifold 30 comprises a gas output port 80 arranged in flow communication with a gas distribution tunnel 85. Three input ports 90A,90B,90C are also disposed in flow communication with gas distribution tunnel 85. Output port 80 is interconnected (via intermediate conduit 66) to a nasal cannula 105 or other known oxygen delivery fixture by an elongate tubular conduit 110 of the type well known in the art for providing COPD patients with their required flow of oxygen. Tubular conduit 110 may be 20 to 30 meters in length.

Each of gas conduits 35A,35B,35C is arranged so that one conduit corresponds to, and extends between, a single output port 70 of input manifold 25 and a single input port 90 of output manifold 30 so as to provide for sealed gas flow communication between input manifold 25 and output manifold 30. Each of gas conduits 35 comprises a tube having an input end interconnected to an output port 70, an output end interconnected to an input port 90, and a needle valve 40 operatively installed in flow control relation with each conduit. It will be understood that at least one, and preferably at least two conduits are used in connection with the present invention. Two of the conduits each also have a solenoid valve 45A,45C operatively installed in flow control relation with the conduit. A coupling 127 is often used to interconnect segments of gas conduits 35 that include needle valves 40 and solenoid valves 45 for ease of assembly. Needle valves 40 and solenoid valves 45 may be selected from any of the well-known prior art valves. For example, a needle valve that has proven to be adequate for use with the present invention is the one manufactured by Deltrol Fluid Products of Bellwood, Ill., model no. EF 10 SS, "Easy Read." A solenoid valve that has proven to be adequate for use with the present invention is the one manufactured by the Honeywell Corporation, and designated as a 2-way, normally open, ⅛ NPT, Type 71215 solenoid valve.

Programmable controller 50 is electrically interconnected to means for monitoring the level of physical activity of a person, such as means for sensing patient motion 10, and provides means responsive to that sensed physical activity for switching solenoids 45A,45C between a first, fully closed state and a second, fully open state. Programmable controller 50 is arranged in operative communication with solenoids 45A,45C and means for sensing patient motion 10, and may be selected from the well know prior art of programmable controllers. For example, a programmable controller that has proven to be adequate for use with the present invention is the Programmable Logic Controller, Catalog No. L16BWA, with hand held programmer, Catalog No. 1761-HHP-B30, manufactured by the Allen-Bradley Corporation, and designated as a Micrologix 1000, with (10) 24V inputs and (6) 120V outputs. It will be understood that other types of programmable devices may be used in connection with the present invention as equivalents to the foregoing programmable controller, such as, a general purpose computer, a personal computer, a specially designed computer or equivalent electronic circuit capable of functioning in substantially the same way, with substantially the same result, as the foregoing programmable controller, or the like programmable means. It will also be understood that an appropriate power supply 130 interconnected, via cable 131, to a source of electrical energy is required to operate the programmable controller or equivalent means, switches, sensors, and solenoids, and will be an obvious design choice for those skilled in the art.

Figure 1:
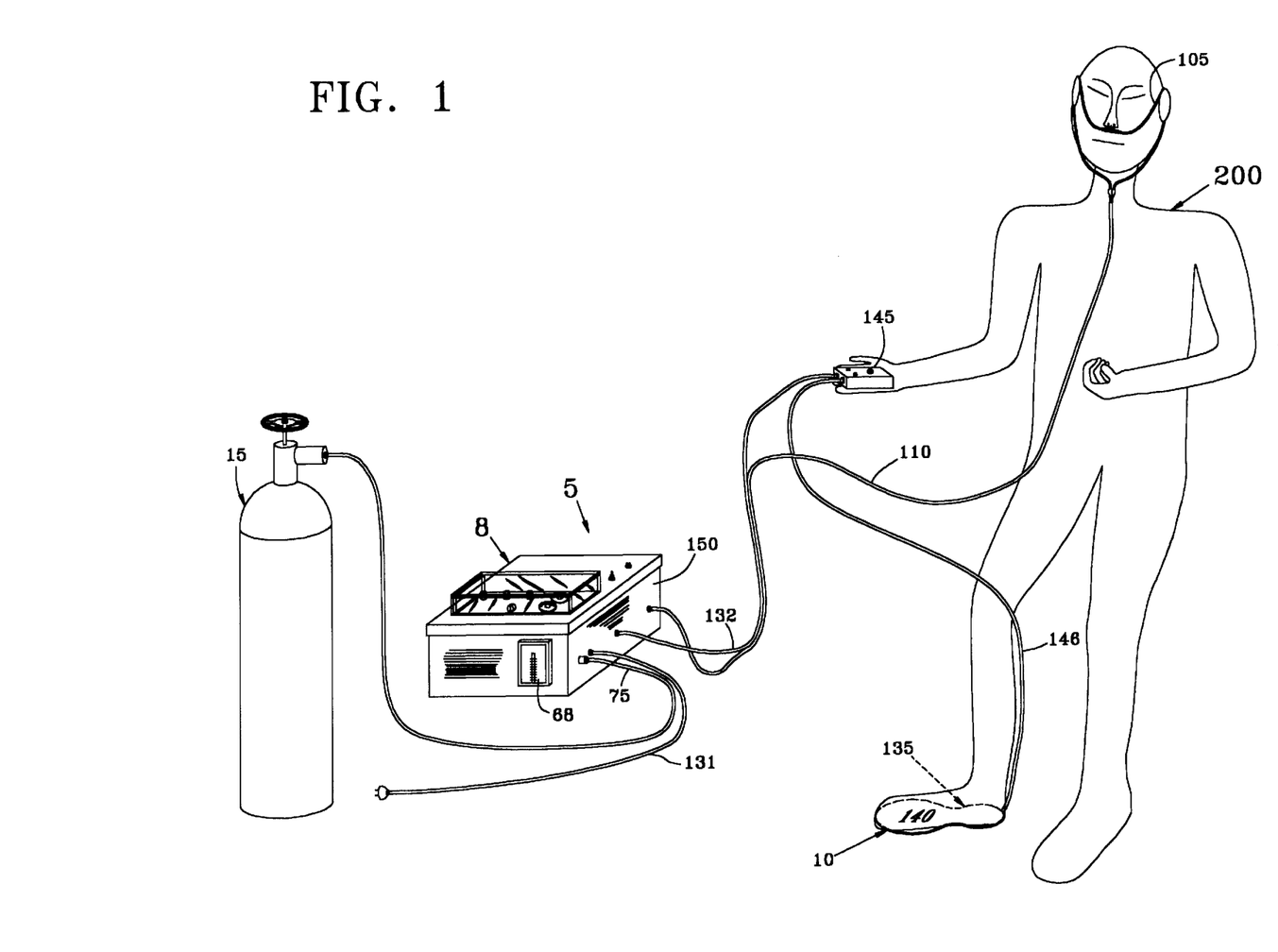
FIG. 1 is a perspective view of an oxygen flow control system formed in accordance with one embodiment of the invention positioned in operative relation to a source of supplemental oxygen and a person in need of such oxygen.

Means for sensing patient motion 10 are operatively interconnected to programmable controller 50, via cable 132, and may include a sensor 135 affixed to a portion of a patient's body, e.g., a foot pad 140 positioned in a slipper or shoe. Sensor 135 may comprise a detector and signal generator, such as a pressure actuated switch, proximity switch, radio control motion sensor, etc., all of the type well known in the art for use in connection with detecting and reporting motion. In a less preferred embodiment of the invention, an oximeter may be substituted for a motion detector. In this way, the blood oxygen level of the patient is monitored directly and appropriate signals are sent to solenoid valves 45A and 45C based on the blood oxygen level detected. It will be understood by those skilled in the art that other types of sensing and monitoring devices may be used in connection with the present invention as equivalents to the foregoing exemplary means for sensing and monitoring the physical activity level of a person, which equivalents are capable of functioning in substantially the same way, with substantially the same result, as the foregoing means for sensing patient motion.

Figure 4:
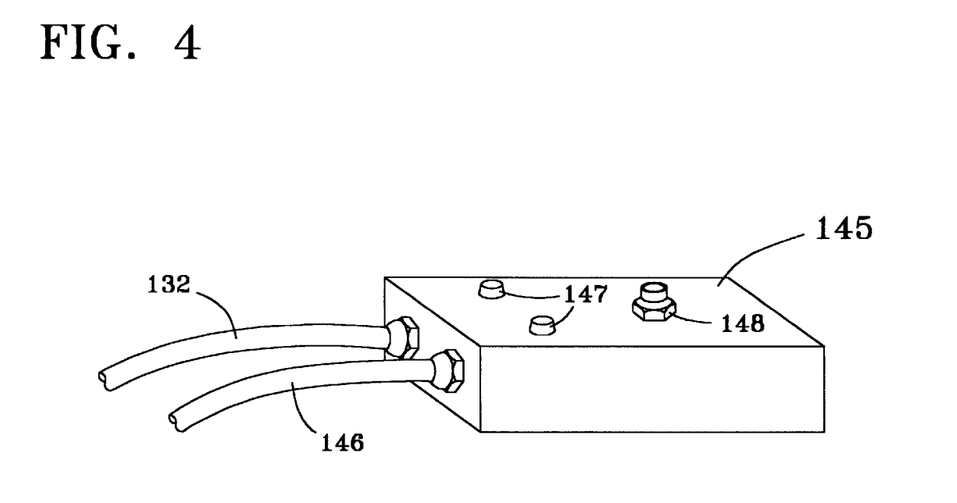
FIG. 4 is a perspective view of a hand control module that may be used in connection with the present invention.

The signals from sensor 135 may be transmitted to programmable controller 50 directly, or a hand held control module 145 may be used to receive signals from sensor 135, via cable 146, or may be used for direct operator/patient input to programmable controller 50. It will be understood that sensor 135 may either emit a radio signal directly to programmable controller 50 each time that the patient's physical activity level increases, or may provide a hard wired electrical signal via cable 146. When using a radio controlled embodiment of the present invention, a small radio receiver may be alternatively positioned within hand control module 145 and adapted to receive the radio signals omitted by sensor 135 and transmit those signals, via cable 132, to programmable controller 50.

In one embodiment of the present invention, sensor 135 comprises an open/close pressure actuated switch (not shown) which is located in foot pad 140. When the patient walks, the pressure switch is actuated, sending one or more signals to programmable controller 50 either directly, via radio transmission, or through hand control module 145, via cable 146. These signals typically represent a measurement of the number of footsteps taken by a patient over a predetermined time period, e.g., 3 to 10 seconds. In response, programmable controller 50 sequentially activates solenoid valves 45A,45C according to a preselected and timed regimen. Programmable controller 50 is adapted to discriminate between spurious signals generated by sensor 135 that are associated with, for example, random movements of the patient, and signals generated by physical exertion associated with walking or changing location.

Referring to FIGS. 1 and 4, hand held module 145 is provided with LED or other readout means 147 and a push button or other actuation means that are interconnected to a single momentary contact switch 148 so that the patient can activate or deactivate the solenoid valves 45A,45C as desired. More particularly, by pressing push button 148 one time, solenoid valve 45A may be opened, increasing the flow of oxygen by one increment. A second actuation of push button 148 will open solenoid valve 45C, which allows the system to operate at the maximum preset oxygen flow rate. A third press of button 148 closes solenoid valve 45C, and a fourth press of button 148 closes solenoid valve 45A, thereby returning the flow rate through the system to the lowest flow rate setting, i.e., the rate of flow allowed via conduit 35B as governed by needle valve 40B. Of course other combinations of manual commands from hand held module 145 or other direct control means may be used in connection with the present invention with equal effect.

Figure 2:
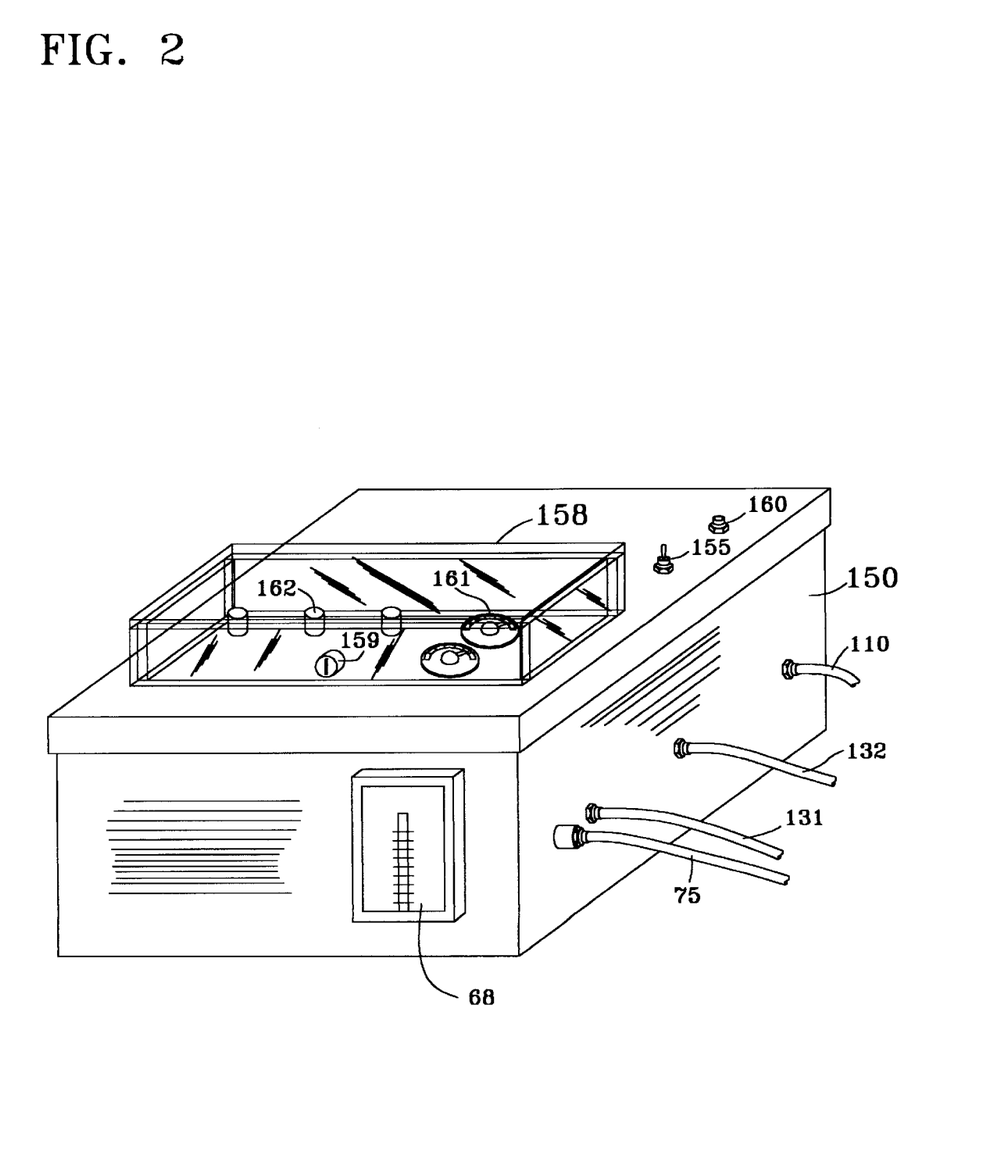
FIG. 2 is a perspective view of the oxygen flow control system cabinet shown in FIG. 1.

Referring to FIGS. 1 and 2, manifolds 25,30, plurality of gas conduits 35, needle valves 40, solenoid valves 45, power supply 130, and programmable controller 50 are preferably disposed in a suitably sized container 150. A power-on/power-off switch 155 and on/off indicator light 160 are positioned on container 150 and operatively interconnected with programmable controller 50. Display panel 68 of oxygen gas flow rate gauge 65 is disposed on the outside surface of container 50 to provide patient 200 with a readily available indication of the oxygen flow rate output by the system of the invention. Manual adjustment means 161, such as turn valves, etc., and indicator lights 162, may be located on the surface of container 150 for access by medical personnel or patient 200. Manual adjustment means 161 may be secured from tampering by a cover plate or box 158, which can be formed from transparent material and locked, via lock 159.

When using the system of the invention, oxygen gas source 15 is normally adjusted to provide the maximum flow of oxygen that has been prescribed for the COPD patient. For example, such patients may often be prescribed a maximum of between 1 and 10 liters per minutes (LPM) of oxygen, and often in the range from about 3.5 to about 4.5 LPM.

Referring to FIG. 3, gas conduit 35B has no solenoid valve associated with it. Needle valve 40B is adjusted so that the minimum flow of oxygen needed by the patient, while at rest, is supplied at all times. Needle valve 40B allows a continuous flow of oxygen, at the prescribed minimum flow rate, no matter what condition is present at programmable controller 50. Thus, in the event of a malfunction in either of solenoid valves 45A,45C (which are normally "open" in an unpowered mode) the minimum flow necessary for the patient will be provided by oxygen flow control system 5, as a "fail-safe".

For example, needle valve 40B may be set to a minimum required flow rate between 0 and 10 LPM (e.g., 2 LPM) by suitable manual adjustment to needle valve 40B. Needle valves 40A and 40C are each separately adjusted so that additional flow volume may be provided to the patient. Thus, if patient 200 requires 2 LPM at rest, but should have available a flow of up to 4.5 LPM during periods of exertion, needle valve 40A may be set to 1 LPM and needle valve 40C may be set to 1.5 LPM. It will be understood that needle valves 40A,40B,40C may be adjusted to provide flow rates between 0 and 10 LPM or more, and the adjustments of each of needle valves 40A,40B,40C may require a "balancing" of the system so that the desired flow rates will be achieved during operation. In some cases, the balancing of the system will require readjustments of each of the needle valves, individually, as they interact with one another in controlling the flow of gas through the system.

Solenoid valves 45A,45C are positioned on conduits 35A and 35C in series with needle valves 40A and 40C. Each solenoid 45A, 45C is under control of programmable controller 50 which is configured to respond to either of two types of input from means for sensing patient motion 10. More particularly, when the patient is at rest and the system is powered-on, solenoid valves 45A and 45C are closed, i.e., in a first state, so as to attenuate the flow of oxygen through conduits 35A and 35C, with the minimum required oxygen flow being allowed through conduit 35B, via needle valve 40B. When additional oxygen is required a solenoid valve, e.g., 45A, is opened, i.e., activated so as to be in a second state, thereby adding an additional 1 LPM of oxygen to the flow through output manifold 30 to patient 200. If further oxygen is required, solenoid 45C is opened adding an additional 1.5 LPM of oxygen to the flow through output manifold 30 to patient 200, bringing the total output of oxygen up to the maximum prescribed of 4.5 LPM. When the system of the invention is not powered, solenoid valves 45A and 45C are always in an "open", full flow configuration as a "fail-safe," so that in the event of a loss of power to the system, oxygen is automatically delivered to the patient at the maximum prescribed level, e.g., 4.5 LPM.

EXAMPLE

Oxygen flow control system 5 operates such that when sensor 135 provides a predetermined number of signals, within a certain number of time intervals, each solenoid 45 is sequentially provided with an instruction from programmable controller 50 to switch from its first (closed) state to its second (open) state, thereby increasing the flow of oxygen to patient 200. For example, a pressure actuated switch located in foot pad 140 may be used to determine the activity level of patient 200 by measuring the number of footsteps, e.g., between one and ten, taken by patient 200 over a preselected first period of time, e.g., between one and sixty seconds, and preferably about six seconds. One or more clocks associated with programmable controller 50 may be used to keep time for the system. Thus for example, for every six second interval, the number of foot switch actuations from foot pad 140 are evaluated by programmable controller 50, and stored in conventional memory means. It should be noted that oxygen flow control system 5 ignores only a single foot switch actuation input sensed during a six second interval, since this may be the result of a random movement of patient 200, and not an actual increase of physical activity level.

If oxygen flow control system 5 receives two or more foot actuation inputs in a six second time period, i.e., patient 200's physical activity level has increased, an instruction is issued by programmable controller 50 to solenoid valve 45A to switch from its first (closed) state to its second (open) state. The actuation of solenoid valve 45A, in turn, opens conduit 35A and adds an additional oxygen flow to patient 200. At the same time, a second clock is started to measure a second predetermined time period, e.g., between one and sixty minutes, and preferably about five minutes, during which solenoid valve 45A will remain open. Thus for example, the 2 LPM of minimum oxygen flow that is always provided to patient 200 is increased by 1 LPM to a total of 3 LPM in order to assist the patient during the increase in physical activity.

If sensor 135 continues to provide signals to programmable controller 50, i.e., the pressure actuated switch located in foot pad 140 continues to be actuated more than once during sequential six second intervals (indicating that the patient's movement is continuing) an instruction is issued to solenoid valve 45C to switch from its first (closed) state to its second (open) state. At the same time, a third clock is started to measure a third predetermined time period, e.g., between one and sixty minutes, and preferably about two minutes, during which solenoid valve 45C will remain open. The actuation of solenoid valve 45C, in turn, opens conduit 35C and adds an additional 1.5 LPM of oxygen flow to patient 200. In this case, patient 200 will be receiving the maximum dosage of oxygen prescribed, i.e., 4.5 LPM.

Advantageously, as long as physical activity is sensed, i.e., as long as the pressure actuated switch in foot pad 140 provides more than one signal to programmable controller 50 within each first timed interval, e.g., six seconds, the instructions to open solenoid valves 45A,45C will be repeated and the respective second and third clocks will be restarted. When the pressure actuated switch located in foot pad 140 fails to provide more than one signal during any given first time interval, an instruction is provided by programmable controller 50 to solenoid valve 45C to switch from its second (open) state to its first (closed) state at the end of its predetermined time period. This corresponds to a first recovery or "ramp-down" period, that may be required by patient 200 after the cessation of physical activity. If the patient continues to remain at rest, yet another instruction is issued, this time to solenoid valve 45A, to switch from its second (open) state to its first (closed) state at the end of its predetermined time period. This will close off flow of oxygen through conduit 35A, and return the flow rate to the minimum prescribed level of 2 LPM.

Alternatively, hand held module 145 may be utilized to allow the patient to have direct control of the opening and closing of solenoid valve 45A and 45C. Hand held module 145 is provided with at least two LED's 147 and push button 148 so that the patient can monitor the flow rate and activate or deactivate solenoid valves as necessary. Thus, if one or more hand switch signals are received by programmable controller 50 from hand control module 145, solenoid valve 45A opens, and one of indicator lights 147 lights up to indicate to patient 200 that solenoid valve 45A has been opened. If two or more additional hand switch signals are received solenoid valve 45C opens increasing the total flow rate to the maximum that is prescribed for patient 200. As this occurs, a second indicator light 147 is also turned on at hand held control module 145.

It should be noted that the hand switch signals are not controlled by clocks, so if solenoid valves 45A, 45C are opened via hand control module 145, they remain open until push button 148 is pressed again. Once this occurs, one or both solenoid valves 45A, 45C may be closed. It should be understood that if signals from hand control module 145 and foot pad 140 overlap each other, solenoid valves 45A, 45C will remain in the second state until all clocks have expired and an additional signal is received from hand control module 145.

It is to be understood that the present invention is by no means limited only to the particular constructions herein disclosed and shown in the drawings, but also comprises any modifications or equivalents within the scope of the claims.

What is claimed is:

1. An oxygen control system for supplying a predetermined rate of flow of oxygen to a person in need of supplemental oxygen during periods of physical activity comprising:

an oxygen source;

an input manifold, an output manifold and a plurality of gas conduits interconnecting said input manifold to said output manifold, wherein said oxygen source is arranged in flow communication with said input manifold and said person is in oxygen flow communication with said output manifold;

a needle valve positioned in flow control relation to each of said plurality of gas conduits so as to control the flow of oxygen from said input manifold to said output manifold;

a plurality of solenoid valves each having a first closed state and a second open state wherein one of said plurality of solenoid valves is positioned in flow control relation to each but one of said plurality of gas conduits;

means for monitoring the level of physical activity of said person; and means responsive to said physical activity monitoring means for sequentially switching said solenoid valves between said first state and said second state.

2. An oxygen flow control system according to claim 1 wherein said solenoids are disposed in said second state when said system is unpowered so that oxygen is free to flow through all of said plurality of gas conduits.

3. An oxygen flow control system according to claim 1 wherein said input manifold comprises a gas input port disposed in flow communication with a gas distribution tunnel and includes three output ports disposed in flow communication with said gas distribution tunnel.

4. An oxygen flow control system according to claim 3 wherein said gas input port is interconnected to said oxygen source by an elongate tubular conduit.

5. An oxygen flow control system according to claim 3 wherein said output manifold comprises a output port arranged in flow communication with a gas distribution tunnel and includes three input ports disposed in flow communication with said gas distribution tunnel, wherein said output port is interconnected to a nasal cannula adapted for delivery of oxygen to said person.

6. An oxygen flow control system according to claim 1 wherein said means for monitoring the level of physical activity comprise a sensor positioned on a portion of a person's body and interconnected to said switching means.

7. An oxygen flow control system according to claim 6 wherein said sensor comprises an open/close pressure switch located in a foot pad portion of a slipper so that when the person walks, said pressure switch is actuated thereby sending signals to said switching means which activates said solenoid valves according to a preselected and timed regimen.

8. An oxygen flow control system according to claim 1 wherein said means for monitoring the level of physical activity comprise a motion detector.

9. An oxygen flow control system according to claim 1 wherein said means for monitoring the level of physical activity comprise a pressure actuated switch.

10. An oxygen flow control system according to claim 1 wherein said means for monitoring the level of physical activity comprise a proximity switch.

11. An oxygen flow control system according to claim 1 wherein said means for monitoring the level of physical activity comprise a radio control motion sensor.

12. An oxygen flow control system according to claim 1 wherein said means for monitoring the level of physical activity comprise a hand held control module for direct input to said switching means.

13. An oxygen flow control system according to claim 1 comprising an oxygen gas flow rate gauge operatively interconnected with said output manifold so as to provide the person with a readily available indication of the oxygen flow rate output.

14. An oxygen control system for supplying a predetermined rate of flow from an oxygen source to a person in need of supplemental oxygen comprising:

an oxygen source;

an input manifold, an output manifold and a plurality of gas conduits interconnecting said input manifold to said output manifold, wherein said oxygen source is arranged in flow communication with said input manifold and said person is in oxygen flow communication with said output manifold;

a needle valve positioned in flow control relation to each of said plurality of gas conduits so as to control the flow of oxygen from said input manifold to said output manifold;

a plurality of solenoid valves each having a first closed state and a second open state wherein one of said plurality of solenoid valves is positioned in flow control relation to each but one of said plurality of gas conduits; and a hand control module interconnected to said solenoids for manually sequentially switching said solenoid valves between said first state and said second state.

15. An oxygen control system for supplying a predetermined rate of flow from an oxygen source to a person in need of supplemental oxygen comprising:

an oxygen source:

an input manifold, an output manifold and three gas conduits interconnecting said input manifold to said output manifold, wherein said oxygen source is arranged in flow communication with said input manifold and output manifold is in oxygen flow communication with said person;

a needle valve positioned in flow control relation to each of said conduits so as to control the flow of oxygen from said input manifold to said output manifold;

a plurality of solenoid valves each having a first closed state corresponding to a preselected level of physical activity of said person and a second, open state corresponding to another preselected level of physical activity of said person, wherein said solenoid valves are positioned in flow control relation to two of said conduits and are disposed in said second state when said system is unpowered so that supplemental oxygen is free to flow to said person;

a pressure actuated switch located in a portion of foot wear worn by said person so that when said person walks, said pressure switch is actuated thereby sending signals to a programmable controller for switching said solenoid valves between said first state and said second state.

16. An oxygen flow control system according to claim 15 wherein said output manifold comprises a output port arranged in flow communication with a gas distribution tunnel and includes three input ports disposed in flow communication with said gas distribution tunnel, wherein said output port is interconnected to a nasal cannula adapted for delivery of oxygen to said person.

17. An oxygen flow control system according to claim 16 wherein each of said gas conduits is arranged so that one conduit corresponds to, and extends between, a single one of said output ports of said input manifold and a single input port of said output manifold so as to provide for gas flow communication between said input manifold and said output manifold.

18. An oxygen control system for supplying a predetermined rate of flow from an oxygen source to a person in need of supplemental oxygen comprising:

an oxygen source;

an input manifold, an output manifold and three gas conduits interconnecting said input manifold to said output manifold, wherein said oxygen source is arranged in flow communication with said input manifold and a nasal cannula is in oxygen flow communication with said output manifold;

a needle valve positioned in flow control relation to each of said three gas conduits so as to control the flow of oxygen from said input manifold to said output manifold;

two solenoid valves each having a first closed state and a second open state wherein one of said solenoid valves is positioned in flow control relation to a first one of said three gas conduits and one of said solenoid valves is positioned in flow control relation to a second one of said three gas conduits;

a sensor capable of detecting the physical activity level of said person and providing a signal that corresponds to said detected physical activity level; and a programmable controller responsive to said signals for sequentially switching said solenoid valves between said first state and said second state.

19. An oxygen control system for supplying a predetermined rate of flow to a person in need of supplemental oxygen during periods of physical activity comprising:

an input manifold, an output manifold and a plurality of gas conduits interconnecting said input manifold to said output manifold, wherein an oxygen source is arranged in flow communication with said input manifold and wherein each of said plurality of gas conduits comprise a tube having an input end sealingly interconnected to said input manifold, and an output end sealingly interconnected to said output manifold, a needle valve positioned in flow control relation to each of said plurality of said gas conduits so as to control the flow of oxygen from said input manifold to said output manifold;

a plurality of solenoid valves each having a first closed state and a second open state wherein one of said plurality of solenoid valves is positioned in flow control relation to each but one of said plurality of gas conduits and wherein one of said plurality of needle valves is operatively installed on each of said gas conduits so as to control the flow of oxygen between said input manifold and said output manifold, and further wherein one of said solenoid valves is operatively installed on each of two of said gas conduits;

means for monitoring the level of physical activity of said person; and means responsive to said physical activity monitoring means for sequentially switching said solenoid valves between said first state and said second state.

* * * * *